's Patent [19]

Stein et al.

[11] 3,955,560
[45] May 11, 1976

[54] IMPLANTABLE NEURAL ELECTRODE

[76] Inventors: Richard B. Stein, 16 Wellington Crescent; Dean Charles, 11583 8D Ave., both of Edmonton, Alberta; Allan Mannard, 4137 Ave. de l'Esplande, Montreal, Quebec, all of Canada

[22] Filed: June 10, 1974

[21] Appl. No.: 477,644

[52] U.S. Cl. ............................ 128/2.1 E; 128/418; 128/DIG. 4; 3/1
[51] Int. Cl.² .................... A61B 5/05; A61N 1/04
[58] Field of Search ............ 128/418, 419 C, 419 E, 128/419 P, 404, 2.06 E, 2.1 E, DIG. 4; 3/1

[56] References Cited
UNITED STATES PATENTS

| | | | |
|---|---|---|---|
| 3,387,608 | 6/1968 | Figar | 128/2.06 E |
| 3,566,233 | 2/1971 | Kahn et al. | 128/2.1 Z |
| 3,646,940 | 3/1972 | Timm et al. | 128/418 |
| 3,718,134 | 2/1973 | Brindley | 128/418 |
| 3,822,708 | 7/1974 | Zilber | 128/418 |
| R26,809 | 3/1970 | Hagfors | 128/418 |

*Primary Examiner*—Robert W. Michell
*Assistant Examiner*—Lee S. Cohen

[57] ABSTRACT

A method and an implantable electrical unit are for use in effecting a direct connection between external apparatus and the nervous systems either to receive information contained in the electrical activity of selected nerve fibers or to transmit thereto information in the form of a stimulating electrical input closely approximating the natural form in order to attain appropriate neural response, in either case with a high degree of discreteness. The method and the unit provide for the regeneration of severed nerve fibers in passageways. The unit includes a member in which the passageways are formed and which is of a material that is electrically non-conductive, and biologically inert and which has electrodes incorporated in the member, each electrode exposed in an appropriate one of the passageways.

12 Claims, 5 Drawing Figures

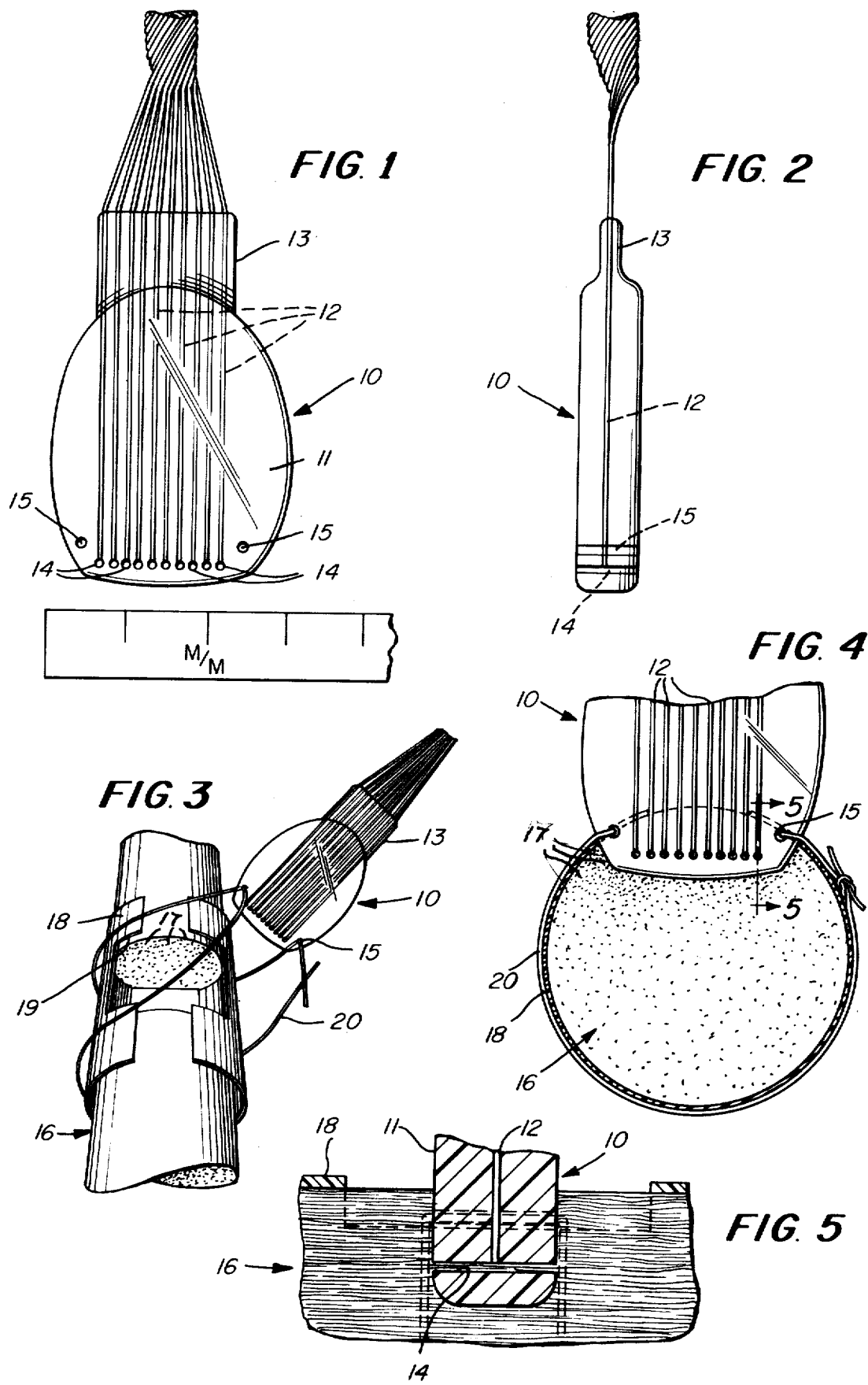

IMPLANTABLE NEURAL ELECTRODE

BACKGROUND OF THE INVENTION

There is need for enabling electrical signals from a number of individual nerve fibers to be simultaneously received or for transmitting thereto signals that the nervous system can decode to produce natural responses, in both cases on a basis that provides a high degree of discreteness, on each of a number of data channels and on a basis that ensures stable operation over months or years with minimal risk to the patient.

As far as we are aware, the human nervous system has been connected to extra-corporeal devices only by gross electrodes placed on the surface of the skin, the brain or peripheral nerves or by microelectrodes placed in the brain or in various peripheral nerves.

Gross electrodes, since they provide a filtered and degraded signal from large masses of nervous or muscular tissue, lack both the discreteness necessary for the smooth and rapid control of multiple joints of a prosthetic limb or for sensory aids which can approach the detail of the natural sense organs. While microelectrodes provide such discreteness, they are very sensitive to movement and must be positioned by manipulators outside the body thereby not only limiting the number of microelectrodes that can be used but also presenting a risk of infection. They are not adapted for use over long periods of time and, additionally, they have high impedance thus requiring careful electrical shielding to prevent the loss of wanted signals in noise.

THE PRESENT INVENTION

The general objective of the invention is to enable electrical signals to be received for processing from or delivered for stimulation to one or more individual nerve fibers simultaneously and independently in freely moving experimental animals and later, in man, in either case, with a high degree of discreteness and on a basis that permits use over a long time, typically providing a multi-channel interface between the nervous system and extra-corporeal devices.

In terms of method, this objective is attained by providing a series of passageways in a material that is a non-conductor of electricity and is biologically inert with each passageway having an electrode exposed therein. A nerve is cut to an extent such that a series of fibers are severed. The passageways are implanted in the cut in a position such that one or more of the severed fibers will regenerate in each of them and form an electrical connection between these fibers and an individual electrode. Thus distinct electrical signals may be recorded from or distinct electrical stimuli may be delivered through each electrode.

In terms of an implant unit, the objectives are attained by providing a member, of material that is a non-conductor of electricity and is biologically inert, with a series of holes that define the passageways and in each of which there is exposed an electrode incorporated in the member. Each passage is of a length and cross-sectional area such that a severed nerve fiber will regenerate therein and is disposed to permit such regeneration when the unit is positioned so that the passageways incorporating the electrodes are in the path or potential path of regenerating fibers.

Although regenerating nerve fibers are particularly mentioned herein, an implant unit may also be positioned in the pathway of nerves during an early stage of an animal's development, i.e., when nerve fibers are initially growing to their ultimate destination. As muscle fibers also produce electrical signals when excited, and, which, like nerve fibers, can be stimulated with external signals, an implant unit may also be incorporated in muscles with muscle fibers registering through its passages. Thus the invention applies to any living animal fibers having electrophysiological properties and undergoing or capable of growth, development, or change and the term "excitable fibers" is used herein to include any such animal fibers.

Yet another objective of the invention is to provide means by which the unit may be secured in place, an objective attained by providing a flexible cuff of material that is a non-conductor of electricity and that is biologically inert, the cuff being dimensioned to be drawn about the nerve and secured by means of sutures, a biologically inert adhesive, or a tie threaded through exposed portions of the member to hold it seated in the cut nerve.

BRIEF DESCRIPTION OF THE DRAWINGS

A preferred embodiment of the invention is illustrated by the drawings with

FIG. 1 is a face view of the implant unit on a substantial increase in scale;

FIG. 2 is an edge view thereof;

FIG. 3 is a somewhat schematic view illustrating a partially severed nerve and one means for securing the implant unit in the cut;

FIG. 4 is a section through the nerve with the implant unit secured by a cuff; and FIG. 5 is a section, on a further increase in scale, taken approximately along the indicated line 5—5 of FIG. 4.

THE PREFERRED EMBODIMENT OF THE INVENTION

The implant unit shown in the drawings in generally indicated at 10 and comprises a member 11 having a series of parallel electrodes 12 embedded therein, the electrodes being appropriate lengths of silver or platinum-irridium wire, the diameter of which, in practice, is 0.003 (76 $\mu$m).

In practice the electrodes 12 are embedded in an epoxy body member which is milled flat on both sides to a thickness in the approximate range of from 0.7 to 1.5 mm. to form the member 11. The member 11 is shown as tear-shaped having a width in the approximate range of from 1.5 to 3.0 mm. and with a neck 13 from which the wires extend. At the opposite end or base of the member 11, there is a transverse series of small holes 14, in practice of a diameter in the order of 10 - 100 $\mu$m, extending from face to face of the member 11. In practice the holes have generally been formed either by mechanical drilling or alternatively by ultrasonically bonding two dissimilar metals (e.g., silver and copper) in the form of a T-junction, and then selectively etching away one of the metals (i.e., copper) with ferric chloride to leave a hole. Numerous other methods are currently available for drilling, bonding, etching or otherwise forming holes of the required dimensions, which may be applied within the terms of the present invention. Two larger holes 15 may be provided close to the edges of the member 11 but spaced above the holes 14.

Referring now to FIG. 3, a nerve, generally indicated at 16 has been cut transversely, to a depth such that a series of its fibers 17 have been severed. The implant unit 10 may then be seated in the cut with the passageways defined by the holes 14 so positioned that each may receive one or more regenerating nerve fibers.

The implant unit 10 is secured in place as by a cuff 18, in practice formed from a section of polyethylene, Teflon, or silastic tubing and is dimensioned to at least partially encircle the nerve 16 with its edges formed with notches 19 of a width to receive the implant unit 10. The position of these notches may be altered so as to facilitate surgical procedure dependent on the anatomy of the region involved. A tie 20 extends through one hole 15 around the cuff 18 on one side of the unit 10 and through the other hole 15 and around the cuff on the other side of the implant unit where the tie is secured by a knot. An alternative method of securing the member 11 in position which is preferable when substantial mechanical forces must be withstood, is by the use of biologically inert adhesives for fixation of member 11 to cuff 18. In addition extra stability may be obtained by suturing the sheath of the nerve 16 to the cuff 18.

In due course, the severed fibers regenerate within the channels or passageways 14. While the dimensions of the implant unit are desirably as small as possible, it should be here noted that the diameter and length of the channels or passageways 14 can be varied to optimize the results for a particular application. The smaller the diameter of the channels or passageways 14 the fewer the number of nerve fibers which will grow through a single channel. Small diameters will increase selectivity in recording and stimulating and will increase signal amplitude. However, small diameters may decrease the probability and reliability of data transmission over long periods of time. The lengths of the channels or passageways must be sufficient to permit normal currents to develop a recordable signal between the exposed electrode 12 and the body fluids and yet short enough to allow nutrients to diffuse between their centers and ends. It will thus be apparent that the dimensions of an implant unit are determined for particular applications by the above requirements to ensure that severed fibers regenerate readily and provide a good connection with the exposed end or terminal of the electrodes.

In practice, the conductors are passed through an implant in the skin that may be of the type shown in United States letters Patent No. 3,663,965. Other methods for coupling signals through the skin by electrostatic or electromagnetic, including inductive, optical, resistive, and radio coupling may be used within the scope of this invention. In addition the signals may be amplified, filtered or modified in other ways inside or outside of the body.

Experimental work with the invention has established that it enables severed nerve fibers to regenerate in the passageways or channels and provide an effective connection with the associated electrodes to enable the electrical activity of each to be transmitted through the skin to a device that may be for research purposes, a prosthetic or other device including sensory aids to be controlled in response to such electrical activity when decoded by suitable processing. In addition, experimental work with the invention has shown that the connection so formed with these nerve fibers is such as to permit selective stimulation of pathways or structures within the living body. Stimulation and recording may be accomplished simultaneously within a single device via the multiple-channel capacity of the device, or through implantation of more than one device. Behavior and thought patterns of a living subject may be determined by the simple experiment of applying a known stimulus pattern at one location and observing the modification which the living system creates on the known input when the output is observed elsewhere. In addition, the incorporation of the living system as one element of a feedback loop facilitates behavioral modification, stimulus reward and punishment training.

For these reasons the invention described has enormous potential for misuse as well as its more obvious and immediate values in rehabilitation medicine. The inventors go on record in this application as being aware of possible misuse of this invention and unanimously declare their opposition to any use of this invention which in any way inhibits the dignity or freedom of any human being. Any use of this system or systems similar to it must include provision for the complete disablement of the system and the return of the human to a normal state. The free will of a human to turn "off" any devices connected to his nervous system must not be interfered with in any way. In addition to the usual purposes for patenting an invention, the inventors intend to establish at this point in time a clearcut precedent for all who follow. The establishment of a policy of non-interference in human individuality, freedom and dignity is essential at this point in the history of the development of interfaces between Man's internal communications systems and mankind's external date systems. The preservation of freedom, privacy, individuality and dignity take precedence over any and all other factors.

We claim:

1. The method of establishing individual connections between a series of electrical conductors and a series of excitable animal fibers, said method comprising the steps of providing a series of passageways in an implant unit of a material that is a non-conductor of electricity and biologically inert, each passageway dimensioned to permit at least one fiber to regenerate therein, providing conductors having electrodes and exposing each electrode in the appropriate one of said passageways, cutting the nerve or muscle containing said fiber to an extent such that the series thereof are severed, and placing the passageways in the cut in a position in which each fiber will regenerate in an appropriate one of them and thus form a connection with the electrode exposed therein.

2. The method of claim 1 in which the diameter of each passageway is in the approximate range of 10 – 100 $\mu$m and the length thereof is in the approximate range of 0.7 to 1.5 mm.

3. The method of claim 1 and the additional step of anchoring the unit to the periphery of nerve or muscle on both sides of the cut therein.

4. An implant unit for use in establishing individual connections between a series of electrical conductors and a series of excitable fibers of a nerve or muscle cut transversely to sever a plurality of its fibers, said implant unit comprising a member of material that is a non-conductor of electricity and is biologically inert, and includes a portion for entry into the cut and having a series of passageways extending completely through it in a position to be within the nerve when the portion is placed in the cut with the series of passageways transversely thereof and the open ends of each passageway disposed to provide potential paths through which the severed fibers may regenerate, the portion being of a thinness such that, when the implant portion is placed in the cut between the ends of said severed fibers, only a few of the severed fibers are in a position in which ingrowth into the implant is inhibited, and electrical conductors within said member each conductor including an electrode portion exposed in the appropriate one of the passageways and a portion extending exteriorly of the member in a position to be exposed when the implant portion is in place, each passageway of a length and cross sectional area such that at least one severed fiber will regenerate therein and form a conductive connection with the electrode portion exposed therein, the ratio of the length of each passageway to its diameter being at least seven.

5. The implant unit of claim 4 in which the thickness implant portion is in the approximate range of 0.7 to 1.5 mm.

6. The implant unit of claim 4 in which the thickness of that portion of the member having the passageways is in the approximate range of 0.7 to 1.4 mm. and the diameter of the passageways is in the approximate range of 10 – 100 $\mu$m so that the ratio of the length of the passageways to their diameters is at least 7.

7. The implant unit of claim 4 in which the member is a molded body from one end of which the conductors extend and the series of passageways extends transversely of its other end, said other end being thicker than said one end.

8. The implant unit of claim 4 and attachable means in the form of a cuff dimensioned to be so disposed that it at least partially encircles the nerve or muscle on both sides of the implant, and means securing the cuff to the nerve or muscle and to the unit member.

9. The implant unit of claim 8 in which the securing means is a biologically inert adhesive.

10. The implant unit of claim 8 in which the securing means are sutures.

11. The implant unit of claim 8 in which the portion of the member that protrudes from the nerve or muscle when the passageways are in position in the cut has laterally extending margins and the cuff is secured thereto.

12. The implant unit of claim 11 in which each laterally extending margin has a hole and a tie extends therethrough and about the cuff.

* * * * *